United States Patent
Vaez-Iravani

(10) Patent No.: US 7,116,413 B2
(45) Date of Patent: Oct. 3, 2006

(54) INSPECTION SYSTEM FOR INTEGRATED APPLICATIONS

(75) Inventor: Mehdi Vaez-Iravani, Los Gatos, CA (US)

(73) Assignee: KLA-Tencor Corporation, San Jose, CA (US)

( * ) Notice: Subject to any disclaimer, the term of this patent is extended or adjusted under 35 U.S.C. 154(b) by 294 days.

(21) Appl. No.: 10/659,556

(22) Filed: Sep. 9, 2003

(65) Prior Publication Data

US 2004/0125368 A1 Jul. 1, 2004

Related U.S. Application Data

(60) Provisional application No. 60/410,717, filed on Sep. 13, 2002.

(51) Int. Cl.
G01N 21/00 (2006.01)

(52) U.S. Cl. .............................. 356/237.2; 356/237.3; 356/237.4; 356/237.5

(58) Field of Classification Search ................... None
See application file for complete search history.

(56) References Cited

U.S. PATENT DOCUMENTS

| | | |
|---|---|---|
| 4,314,763 A | 2/1982 | Steigmeier et al. |
| 4,378,159 A | 3/1983 | Galbraith |
| 4,391,524 A | 7/1983 | Steigmeier et al. |
| 4,423,331 A | 12/1983 | Koizumi et al. |
| 4,479,714 A | 10/1984 | Lehrer |
| 4,508,450 A | 4/1985 | Ohshima et al. |
| 4,523,841 A | 6/1985 | Brunsting et al. |
| 4,526,468 A | 7/1985 | Steigmeier et al. |
| 4,598,997 A | 7/1986 | Steigmeier et al. |
| 4,735,504 A | 4/1988 | Tycko |

(Continued)

FOREIGN PATENT DOCUMENTS

JP 63-14830 1/1988

(Continued)

OTHER PUBLICATIONS

"Requirements for Future Surface Inspection Equipment for Bare Silicon Surfaces," P. Wagner et al., Wacker-Chemitronic GmbH, Burghausen, Germany, W. Baylies, BayTech Group, Weston Massachusetts.

(Continued)

Primary Examiner—Michael P. Stafira
(74) Attorney, Agent, or Firm—Parsons Hsue & de Runtz LLP

(57) ABSTRACT

A compact surface inspection optical head is disclosed which comprises a frame with two rings of apertures therein. The first set of apertures surrounding and close to a normal direction to the surface to be inspected is connected to fibers used to collect scattered radiation useful for the detection of micro-scratches caused by chemical and mechanical polishing. Where the position of these apertures is selected to be away from patterned scattering or diffraction, these apertures and their associated fibers may be useful for anomaly detection on patterned surfaces. A second ring of apertures at low elevation angles to the surface inspected is connected to fibers to collect radiation scattered by the surface inspected for anomaly detection on patterned surfaces. This ring of apertures segments azimuthally the collection space so that the signal outputs from detectors that are saturated by the pattern diffraction or scattering may be discarded and only the outputs of unsaturated detectors are used for anomaly detection. A pair of larger apertures in the double dark field positions may be employed for anomaly detection on unpatterned surfaces. Scattered radiation passing through the two larger apertures may be collected by objectives or fiber bundles.

92 Claims, 3 Drawing Sheets

U.S. PATENT DOCUMENTS

| | | | |
|---|---|---|---|
| 4,744,663 | A | 5/1988 | Hamashima et al. |
| 4,794,265 | A | 12/1988 | Quackenbos et al. |
| 4,893,932 | A | 1/1990 | Knollenberg |
| 4,898,471 | A | 2/1990 | Stonestrom et al. |
| 4,929,845 | A | 5/1990 | Amir et al. |
| 5,076,692 | A | 12/1991 | Neukermans et al. |
| 5,108,176 | A | 4/1992 | Malin et al. |
| 5,153,668 | A | 10/1992 | Katzir et al. |
| 5,189,481 | A | 2/1993 | Jann et al. |
| 5,270,794 | A | 12/1993 | Tsuji et al. |
| 5,315,609 | A | 5/1994 | Tanaka et al. |
| 5,377,001 | A | 12/1994 | Malin et al. |
| 5,377,002 | A | 12/1994 | Malin et al. |
| 5,389,794 | A | 2/1995 | Allen et al. |
| 5,406,367 | A | 4/1995 | Sopori |
| 5,416,594 | A | 5/1995 | Gross et al. |
| 5,424,838 | A | 6/1995 | Siu |
| 5,530,550 | A | 6/1996 | Nikoonahad et al. |
| 5,650,614 | A | 7/1997 | Yasutake et al. |
| 5,798,829 | A | 8/1998 | Vaez-Iravani et al. |
| 5,798,831 | A | 8/1998 | Hagiwara |
| 5,864,394 | A | 1/1999 | Jordan, III et al. |
| 6,088,092 | A * | 7/2000 | Chen et al. .............. 356/237.2 |
| 6,104,945 | A | 8/2000 | Modell et al. |
| 6,201,601 | B1 | 3/2001 | Vaez-Iravani et al. |
| 6,271,916 | B1 | 8/2001 | Marxer et al. |
| 6,538,730 | B1 | 3/2003 | Vaez-Iravani et al. |

FOREIGN PATENT DOCUMENTS

| | | |
|---|---|---|
| JP | 63-140904 | 6/1988 |
| JP | 62-85449 | 11/1998 |
| WO | 9615354 | 9/1996 |
| WO | WO 00/00873 | 1/2000 |
| WO | WO 00/00874 | 1/2000 |
| WO | WO 00/02037 | 1/2000 |

OTHER PUBLICATIONS

"The Importance of Media Refractive Index in Evaluating Liquid and Surface Microcontamination Measurements," R. Knooenberg et al., *The Journal of Environment Sciences*, Mar./Apr. 1987.

"Surface Inspection System for Estimation of Wafer," Y. Yatsugake et al., *Hitachi Engineering Technical Report*, vol. 11, Jan. 1996, pp. 21-26 (with translation).

Figure, Hitachi Electronics Engineering Co., Ltd., presented by Etsuro Morita of Mitsubishi Materials Silicon Corp. in a presentation entitled "Exploration of COP and COP Defect Crystal Originated 'Particles'," at the 6th International Workshop on 300 mm wafers on Dec. 5, 1996 in Makuhari, Japan.

"Notification of Transmittal of the International Search Report or the Declaration" corresponding to PCT/US03/28593, filed Sep. 10, 2003, 6 pages.

* cited by examiner

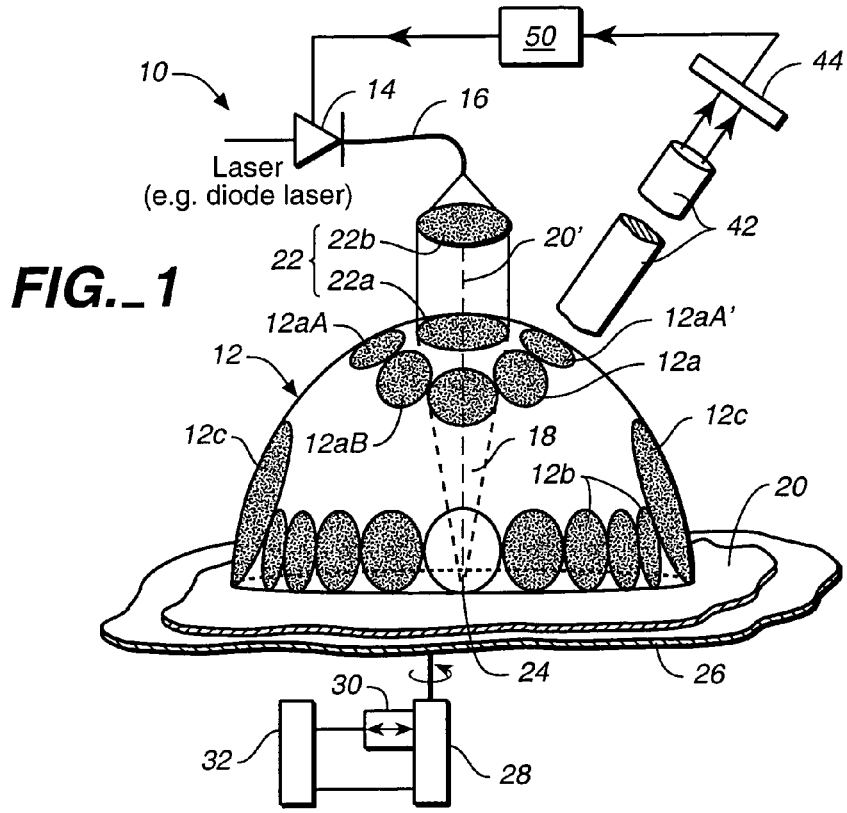
FIG._1
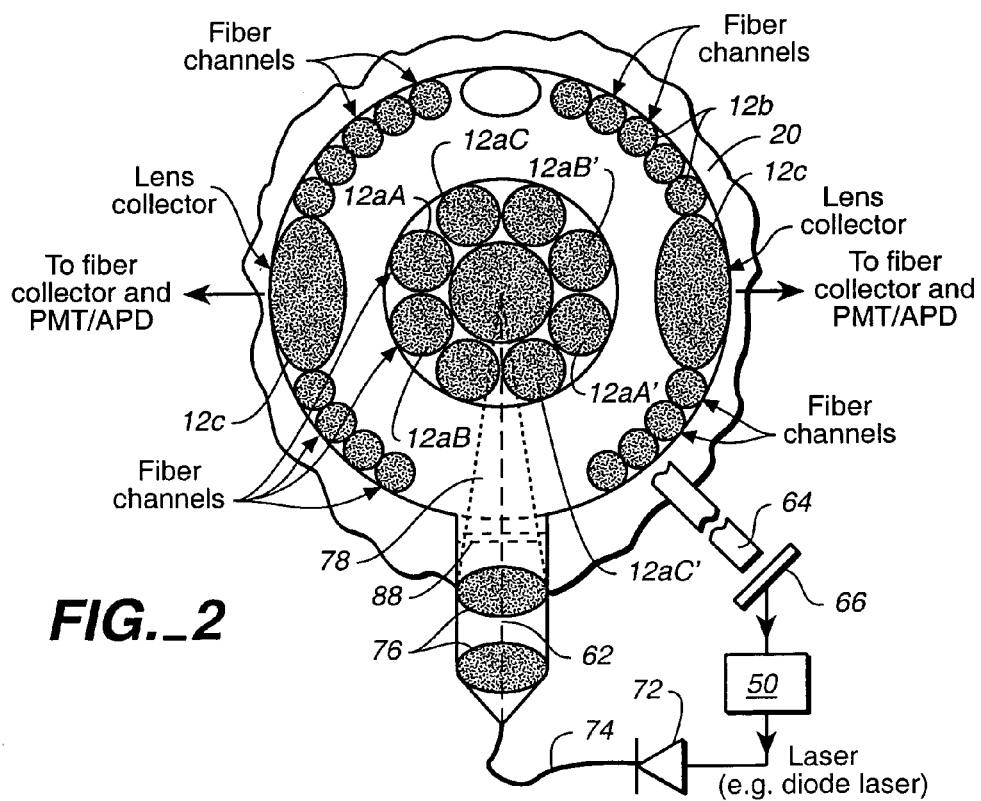
FIG._2

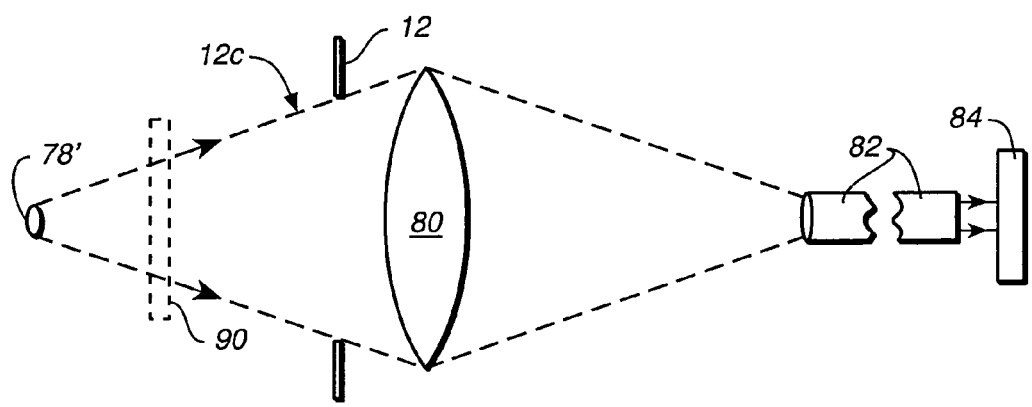
FIG._3
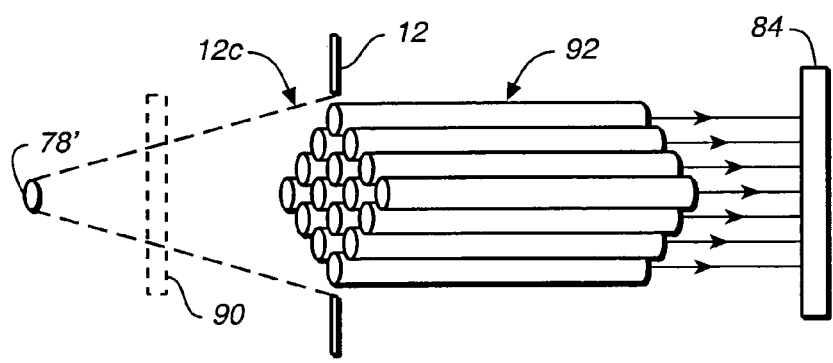
FIG._4

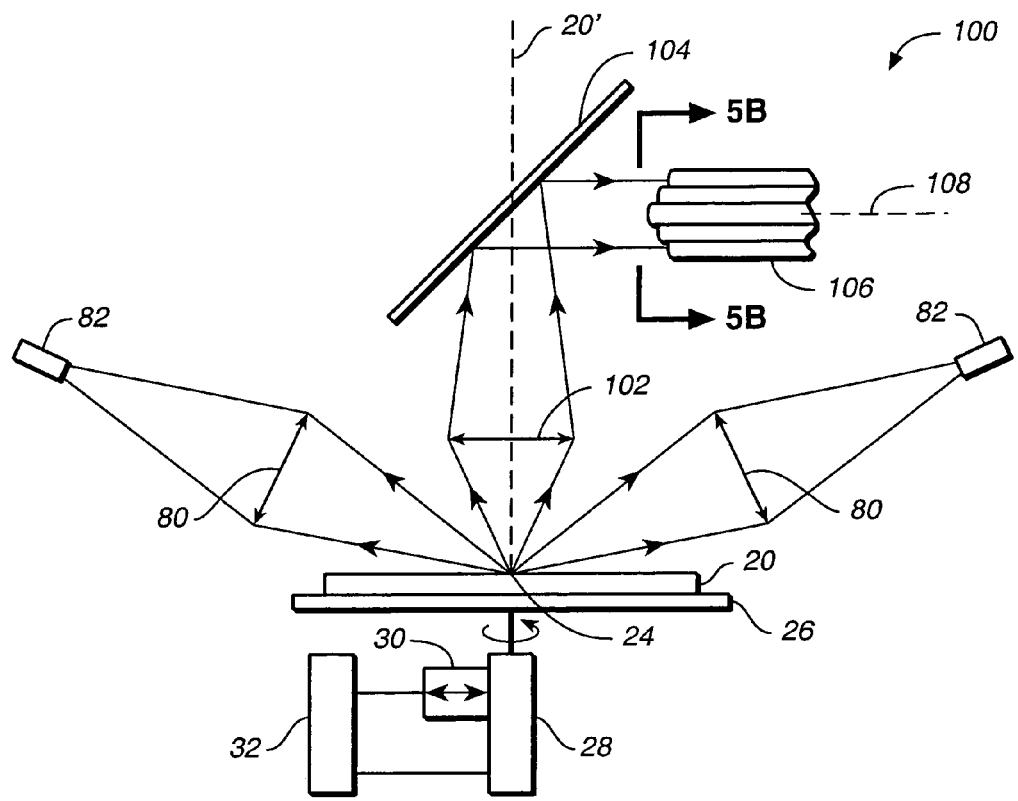
FIG._5A
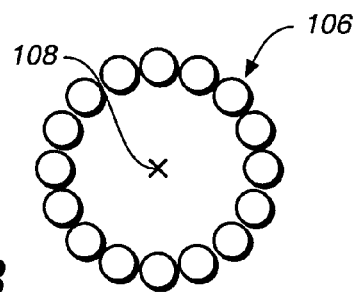
FIG._5B
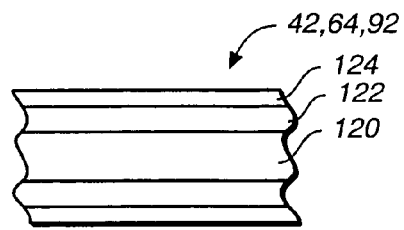
FIG._6

INSPECTION SYSTEM FOR INTEGRATED APPLICATIONS

CROSS-REFERENCE TO RELATED APPLICATION

This application claims the benefit of U.S. Provisional Patent Application No. 60/410,717 filed Sep. 13, 2002; this application is related to U.S. patent application Ser. No. 09/828,269, filed Apr. 6, 2001, now U.S. Pat. No. 6,538,730; application Ser. No. 09/828,492, filed Apr. 6, 2001, abandoned; and application Ser. No. 08/933,771, filed Sep. 19, 1997, now U.S. Pat. No. 6,201,601. The related applications and patents are incorporated herein by reference in their entireties.

BACKGROUND OF THE INVENTION

This invention relates in general to defect detection, and, in particular, to an improved system for detecting anomalies on surfaces, such as particles and surface-originated defects such as crystal-originated particles ("COPs"), surface roughness and micro-scratches.

The SP1$^{TBI}$™ detection system available from KLA-Tencor Corporation of San Jose, Calif., the Assignee of the present application, is particularly useful for detecting defects on unpatterned semiconductor wafers. While the SP1$^{TBI}$ system provides unsurpassed defect sensitivity on bare wafers or unpatterned wafers, this is not the case when it is used for inspecting wafers with patterns thereon such as wafers with memory arrays. In this system, all of the radiation collected by a lens or ellipsoidal mirror is directed to a detector to provide a single output. Thus, since pattern on the wafer will generate Fourier and/or other strong scattering signals, when these signals are collected and sent to the detector, the single detector output becomes saturated and unable to provide information useful for detecting defects on the wafer.

Conventional techniques for detecting defects on wafers are either tailored for the inspection of patterned wafers, or for inspecting unpatterned or bare wafers, but not both. While inspection systems for detecting patterned wafers may also be used for inspecting unpatterned wafers, such systems are typically not optimized for such purposes. Systems designed for the inspection of unpatterned or bare wafers, on the other hand, may have difficulties handling the diffraction or other scattering caused by the patterned structures on patterned wafers, for reasons such as those explained above.

For the inspection of patterned wafers, entirely different inspection systems have been employed. One commercial system, known as AIT™ inspection system, is available from the Assignee of the present application, KLA-Tencor Corporation of San Jose, Calif.; such system is also described in a number of patents, including U.S. Pat. No. 5,864,394. In the AIT system, spatial filters are employed to shield the detectors from the diffraction or scattering from the patterned structures on the wafer. The design of such spatial filters can be based on prior knowledge of the patterned structures and can be quite complex. Furthermore, this system utilizes a die to die comparison process in order better to identify the presence of a defect.

None of the above-described instruments is entirely satisfactory for the inspection of patterned wafers. It is therefore desirable to provide an improved defect detection system for patterned wafers in which the above difficulties are alleviated. To further economize on the space required for inline inspection, it is desirable to provide an instrument that can be optimized for both unpatterned and patterned wafer inspection.

Chemical mechanical planarization (CMP) has gained wide acceptance in the semiconductor industry. The CMP process, however, also creates many types of defects that can significantly impact the yield of an integrated circuit (IC) device if the defects are not properly controlled. Among the CMP defects, the micro-scratch has a strong impact on IC yield. Therefore, it is desirable to be able to detect and differentiate micro-scratches and other CMP defects from particles.

U.S. patent application Ser. No. 09/828,269 describes a defect detection system employing a collector that comprises a curved mirror such as the mirror ellipsoidal in shape. While such system is versatile and desirable for many applications, there may be applications where the use of such curved mirrors may be too expensive or impractical, such as where it is desirable for the defect detection system to be very small. It is therefore desirable to provide an improved system for such applications.

SUMMARY OF THE INVENTION

One aspect of the present invention is directed towards an inspection apparatus where a first and/or a second beam of radiation is supplied by a source to a surface, where the first beam is substantially normal to the surface and the second beam is at an oblique angle to the surface. Optical devices disposed at different azimuthal angles about a reference direction are positioned so that radiation scattered by the surface at different azimuthal angles with respect to a line normal to the surface is directed to different devices without using a common collecting instrument to direct the scattered radiation. A collector substantially in a double dark field arrangement relative to the second beam is employed where the collector has an aperture that is larger than any one of the optical devices. This collector also collects radiation scattered by the surface.

The above-described apparatus is versatile and can be used for detecting anomalies on different types of surfaces, including patterned surfaces such as semiconductor wafers with memory arrays or logic thereon, unpatterned surfaces such as bare wafers, and for detecting anomalies resulting from chemical and mechanical polishing of semiconductor wafers. The apparatus can also be made compact so that it is particularly adapted for integration with processing equipment. Since a common collecting instrument, such as the ellipsoidal mirror of the related applications, is not used to direct scattered radiation to the optical devices, the apparatus can be made at a lower cost and more compact while retaining the above-described versatile capabilities.

The above-described apparatus can be operated for detecting anomalies on different types of surfaces. In operation, the source is caused to supply the first and/or second beam to the surface. The surface is caused to be scanned by the beam. Radiation scattered by the surface is directed to the optical devices without employing a common collecting instrument. The radiation scattered by the surface and collected by the devices and/or the at least one collector is detected, and anomalies on different types of surfaces are determined from the detected radiation.

BRIEF DESCRIPTION OF THE DRAWINGS

FIG. 1 is a side perspective view of a surface inspection apparatus useful for illustrating an embodiment of the invention.

FIG. 2 is a top view of a portion of the apparatus of FIG. 1.

FIG. 3 is a schematic view of a portion of the apparatus of FIGS. 1 and 2 illustrating in more detail a collector in a double dark field arrangement to illustrate one embodiment of the invention.

FIG. 4 is a schematic view of a collector in a double dark field arrangement illustrating an alternative embodiment of the invention.

FIG. 5A is a schematic view of a surface inspection apparatus to illustrate an alternative embodiment of the invention.

FIG. 5B is a schematic view of a possible arrangement of multiple fiber channels for carrying scattered radiation in the embodiment of FIG. 5A.

FIG. 6 is a cross-sectional view of a portion of an optical fiber that is useful in the embodiment of the invention.

For simplicity in description, identical components are labeled by the same numerals in this application.

DETAILED DESCRIPTION OF THE EMBODIMENTS

FIG. 1 is a side perspective view of a surface inspection apparatus useful for illustrating one embodiment of the invention. As shown in FIG. 1, apparatus 10 comprises a housing preferably in the shape of a hemi-sphere 12 with a number of apertures. Frames, shells or housings with other shapes or construction (e.g. a frame constructed from elongated strips of material) that would serve essentially a similar function may be used and are within the scope of the invention. A radiation source 14 such as a laser (e.g., diode laser) supplies radiation through an optical channel such as an optical fiber 16 for illuminating the surface of the sample such as a semiconductor wafer 20. While the embodiments herein are illustrated by reference to inspection of semiconductor wafers, it will be understood that the invention is applicable to other samples as well, such as flat panel displays and magnetic and optical disks or read/write heads and other types of samples. The radiation supplied by source 14 may be monochromatic, polychromatic or broadband. Radiation from the optical fiber 16 is focused by a lens system 22 to a spot 24 on the top surface of sample 20. As shown in FIG. 1, objective or lens 22a of system 22 may be conveniently supported by frame 12, where objective 22a sits within an aperture in the frame. Wafer 20 is supported on the chuck 26 which is rotated by a means of a motor 28 and translated in a direction by gear 30 so that beam 18 illuminates spot 24 which is caused to move and trace a spiral path on the surface of wafer 20 to inspect the surface of the wafer. Motor 28 and gear 30 are controlled by a controller 32. Alternatively, the beam 18 and frame 12 may be caused to move in a manner known to those skilled in the art to trace the spiral path. As still another alternative, either the chuck 26 or the frame 12 and beam 18 may be caused to move along straight lines to scan straight line segments in a zigzag or serpentine path. Still other alternatives involve moving both the wafer 20 and the beam 18 and frame 12 so that the relative motion between them is along any one of the paths described above. All such variations are within the scope of the invention.

As shown in FIG. 1, frame 12 defines therein or is constructed to permit attachment to devices defining two sets of apertures: 12a and 12b. For example, and as described below, the apertures may be defined by ends of optical fibers, such as the end of fiber 42. The apertures 12a are located near a normal direction 20' to the surface of sample 20 and passing through the spot 24. Radiation scattered by the portion of the surface within the illuminated spot 24 passes through the set of apertures 12a to reach a set of collectors. In one embodiment, optical fibers may be used as the collectors. One example of such type of collectors is illustrated by optical fiber 42, where the fiber conveys the radiation scattered by the surface through corresponding aperture 12aA' within the set of apertures 12a to a corresponding detector 44. To simplify the figure, only one such fiber and only one such detector are shown; it being understood that each of at least some of the remaining apertures 12a may also have a corresponding collector optical fiber and corresponding detector for detecting the radiation scattered by the surface and passing through such aperture. Preferably the fibers such as 42 are disposed symmetrically about the normal direction 20'. The detectors then generate output signals in response to the collected scattered radiation passing through the set of apertures 12a and sends the output signals to a processor 50.

As known to those skilled in the art, semiconductor wafer processing frequently involves chemical and mechanical polishing ("CMP") which may cause micro-scratches on the surface of the wafer. The set of apertures 12a and the corresponding fibers and detectors are suitable for detecting such micro-scratches. Thus, when spot 24 is illuminated by a beam 18 having an axis substantially along the normal direction 20', apertures 12a and their corresponding fibers located to collect radiation scattered close to the normal direction are suitable for detecting such micro-scratches. To detect the micro-scratches, preferably the illumination beam is substantially normal to the surface inspected; nevertheless, for some applications, the illumination beam may be supplied at an oblique angle to the surface inspected for the detection of micro-scratches caused by chemical or mechanical polishing. Such and other variations are within the scope of the invention. Preferably, the apertures in the first set 12a collect radiation scattered by the surface at angles between about 10 to 30 degrees from the normal direction 20', and the first set 12a comprises 6 to 10 apertures.

For detecting micro-scratches, it may be useful for processor 50 to compare pairs of signals that are derived from radiation scattered along directions that are opposite to each other across the normal direction 20'. Thus, for example, apertures 12aA and 12aA' in set 12a are located on the opposite sides of the normal direction 20'. Apertures 12aB and 12aB' are located on the opposite sides of the normal direction 20' as shown more clearly in FIG. 2. Because micro-scratches tend to scatter radiation more strongly in planes that are perpendicular to the direction of the micro-scratches rather than in directions that are parallel to it, comparing the signals derived from radiation scattered and collected by oppositely situated pairs of apertures and fibers may be useful for detecting such micro-scratches. FIG. 2 is a top view of apparatus 10 of FIG. 1. Thus, in reference to FIG. 2, it may be useful for microprocessor 50 to compare the signals from the detectors detecting radiation scattered and collected through apertures 12aA, 12aA' to the signals derived from radiation scattered and collected through apertures 12aC, 12aC'. It may also be useful to compare the signals derived from radiation scattered by the surface and collected through each pair of oppositely situated apertures, such as 12aA and 12aA'. The detection of micro-scratches as described above may be carried out simultaneously or sequentially with the detection of other anomalies on the surface of the sample 20.

Instead of using optical fibers such as fiber 42 to collect and convey the radiation scattered by the surface and passing through the corresponding aperture to the detector 44, the detector may be placed directly in or near a corresponding aperture for detecting such scattered radiation. The advantage of using optical fibers to collect and convey the radiation to detectors is that this permits the portion of apparatus 10 that is positioned close to sample 20 to be of a particularly compact design. Thus, in one embodiment, an optical head comprising frame 12 and lens system 22 has horizontal dimensions (that is, in a plane parallel to surface of wafer 20) that do not exceed about 5 cm. For detecting micro-scratches, the aperture in the first set 12a preferably form a ring around the normal direction 20'. In one embodiment, the set 12a includes six to ten apertures with the same number of corresponding optical fibers and detectors. Apertures 12a and their corresponding fibers and detectors may also be useful for the detection of anomalies other than micro-scratches, such as particles and surface or subsurface defects on patterned or unpatterned semiconductor wafers. As shown in FIGS. 1 and 2, in addition to the first set of apertures 12a, another set of apertures 12b is defined in frame 12 for passing radiation scattered by the surface in the illuminated spot 24 at collection angles that are close to the surface of the wafer 20. Preferably, the apertures 12b collect radiation scattered by the surface at a low elevation angle, such as angles of between about 10 and 40 degrees to the top surface of wafer 20.

As shown more clearly in FIG. 2, in addition to or in lieu of illuminating wafer 20 in a direction substantially normal to the surface of the sample, the sample can also be illuminated along an optical axis 62 at an oblique angle to the surface of the wafer. The chuck 26 has been omitted in FIG. 2 to simplify the figure.

As in the case of the first set of apertures 12a, each of at least some of the apertures in the second set 12b has a corresponding optical fiber, such as fiber 64, positioned to collect the radiation scattered by the surface within the illuminated spot 24 and passing through such aperture. Fiber 64 then conveys the radiation collected to a corresponding detector 66 which provides an output signal in response thereto. To simplify FIG. 2, only one optical fiber 64 collecting scattered radiation passing through one of the apertures in the second set 12b is shown with its corresponding detector 66; it being understood that more fibers and corresponding detectors are employed typically in the embodiment of FIGS. 1 and 2. To provide the beam at an oblique angle to the sample, a radiation source such as a laser (e.g., diode laser) 72 may be used which supplies radiation through a fiber 74 and a lens system 76 to provide beam 78 along the optical axis 62 at an oblique angle to the surface of wafer 20. Illuminating the sample surface at an oblique angle is particularly advantageous for the detection of anomalies on patterned or unpatterned wafers. For detection of anomalies on unpatterned wafers or bare wafers, it would be desirable to collect radiation scattered by the surface within larger collection angles so as to increase the amount of signal that may be detected. For this purpose, in addition to the second set of collection apertures 12b, one and preferably two larger collection apertures 12c may be employed in a double dark field arrangement as shown in FIG. 2. Dark field systems are those where the radiation collected is that scattered by the sample and collected along collection paths that are away from the specular reflection direction from the sample surface of the illumination beams. Dark field systems are explained in more detail in "Wafer Inspection Technology Challenges for ULSI Technology", by S. Stokowski and M. Vaez-Iravani, Proceedings of conference on Characterization and Metrology for ULSI Technology, Edited by D. G. Seiler, A. C. Diebold, W. M. Bullis, T. J. Shaffner, R. McDonald, and E. J. Walters, American Institute of Physics, PP. 405–415 (1998).

A double dark field configuration or arrangement is where the optical axis of the collection aperture is at a location substantially at +90° or −90° azimuthal angle relative to the illumination beam as the beam reaches the surface. Azimuthal angle refers to the angle made by the measuring or detection direction to a reference direction when viewed from the top. Thus, in reference to FIG. 2, the two apertures 12c have optical axes substantially at +90° and −90° azimuthal angle relative to the illumination beam 78 as the beam reaches the surface of the sample 20. As shown in FIGS. 1 and 2, the collection aperture 12c is larger, and preferably much larger, than the apertures in the first and second sets 12a, 12b. In such event, the collection and detection of radiation passing through the larger apertures 12c may be adequate for detecting defects of unpatterned surfaces such as those of semiconductor wafers. Frame 12 is preferably made of a material so that the radiation scattered by the surface and reaching the frame would not be reflected or scattered back towards the surface or towards any of the apertures. In one embodiment, frame 12 is made of a transparent material so that radiation scattered by the surface is transmitted through the frame rather than being reflected or scattered thereby. In another embodiment, frame 12 is made of a material with a radiation absorbent surface such as a surface that is anodized. Such and other variations are within the scope of the invention.

In one embodiment of the invention, where the surface to be inspected is unpatterned (such as a bare wafer), illumination is supplied by beam 78 at an oblique angle to the surface and radiation scattered by the illuminated spot on the surface of wafer 20 and passing through apertures 12c is collected by an objective in the manner shown in FIG. 3. As shown in FIG. 3, radiation scattered by the illuminated spot 78' on the surface of wafer 20 by beam 78 and passing through the aperture 12c is focused by objective or lens 80 towards an optical fiber 82. The radiation collected by fiber 82 is then conveyed to a detector 84. The same configuration may be employed to collect and detect radiation scattered and passing through each of the apertures 12c at +90° and −90° azimuthal angles relative to beam axis 62.

Where the unpatterned surface is smooth, it may be desirable to supply a beam 78 which is P-polarized and detect unpolarized radiation as shown in FIG. 3. For this purpose, a laser diode 72 may be selected to supply such radiation or a polarizer 88 may be employed, causing the beam 78 to be P-polarized. Where the unpatterned sample 20 has a rough surface, it may be desirable to supply a beam 78 which is S-polarized and to detect only S-polarized radiation that is scattered. For this purpose, the laser diode 72 may be selected to supply such radiation or polarizer 88 may be oriented to pass only S-polarized radiation in beam 78. In order to detect S-polarized radiation, another polarizer 90 shown in phantom in FIG. 3 may be employed so that the radiation detected by detector 84 is in response only to the S-polarized components of the scattered radiation from the illuminated spot 78'.

Instead of employing an objective or lens 80 to collect the radiation scattered from spot 78', a bundle 92 of optical fibers may be employed instead as shown in FIG. 4.

Where sample 20 is a dielectric film, it may be desirable to supply circularly polarized radiation to illuminate the sample 20 while unpolarized radiation is detected. For this purpose, diode 72 supplies circularly polarized radiation and the member 88 may instead be a blank so that beam 78 comprises only circularly polarized radiation.

While in many applications, anomalies on unpatterned surfaces may be advantageously detected by means of the double dark field arrangements shown in FIGS. 3 and 4, there are certain applications where the use of the second set of fibers 12*b* may be advantageous with oblique illumination of the sample. Thus, for certain types of unpatterned surfaces, detection of radiation scattered by the surface within one or more predetermined azimuthal angle(s) may be advantageous so that the signals generated by detectors in response to only such collected radiation may be meaningful. In such event, the detector output(s) generated in response to radiation collected within such predetermined azimuthal collection angle(s) may be used for determining whether there are anomalies on such surfaces. Preferably, the detector output(s) generated in response to radiation that are collected outside such predetermined azimuthal collection angle(s) are not used for determining whether there are anomalies on such surfaces.

As noted above, the collection angles subtended at the center of illuminated spot 78' by apertures 12*c* are preferably larger than those of apertures 12*a* or 12*b*. In one embodiment, at least one of the two apertures 12*c* subtends a collection angle of about 20 to 60 degrees at the center of illuminated spot 78'. In another embodiment, at least one of the apertures 12*c* subtends a collection angle of about 40 to 60 degrees at the center of the spot 78'.

If the laser diode 72 selected is one that provides polarized radiation such as P- or S-polarized or circularly polarized radiation, optical fiber 74 is preferably a single mode fiber. In contrast, fibers used for conveying the collected scattered radiation from the surface, such as fibers 42, 64, 82 and 92 may be multimode fibers. To simplify the figures, the connection between detectors such as detector 84 and processor 50 of FIGS. 1 and 2 are not shown in FIGS. 3 and 4.

Processor 50 then processes the output signals of detectors 84 in order to determine the presence of anomalies on unpatterned surfaces (and on patterned surfaces as well, as will be described below).

Instead of using two laser diodes 14 and 72, a single laser diode may be employed where the radiation emitted by the diode is supplied via two different optical fibers 16 and 74 to supply the two beams 18 and 78 shown in FIGS. 1 and 2. For a compact integrated design, lens 80 in FIG. 3 may be connected directly to frame 12 at aperture 12*c*. Alternatively, and as shown in FIG. 4, no lens is required in the integrated optical head which comprises only frame 12 and the objective system 22 and/or the objective system 76, receiving radiation supplied via optical fibers 16 and 74. Scattered radiation passing through the apertures may then be conveyed through fibers such as fibers 42, 64 and 92 to corresponding detectors.

The apparatus illustrated in FIGS. 1 and 2 may also be advantageously used for detecting anomalies on patterned surfaces, such as patterned semiconductor wafers. The pattern on such surfaces would diffract radiation, and the detectors receiving such radiation may become saturated. Since the collection space of the scattered radiation is segmented by means of the two sets of fibers 12*a*, 12*b* in both the azimuthal (horizontal plane) and elevation (vertical plane) directions, the saturation of some detectors will leave the remaining detectors still yielding output signals useful for detecting anomalies. An elevation angle refers to the angle made by a measurement or detection direction to the surface of the sample inspected for anomalies in a vertical plane containing the measurement or detection direction. In other words, if a particular aperture in the two sets 12*a* and 12*b* collects radiation which is diffracted or scattered by pattern, it is likely that the detector connected to the aperture by a fiber will become saturated. However, an aperture next to such aperture may be situated so that it does not receive any scattering or diffraction from pattern so that the scattered radiation that it collects and the detector output signal that results may be used for detection of anomalies. Thus, in one embodiment, where sample or wafer 20 inspected has a patterned surface, processor 50 would discard the output signals of detectors that are saturated and determine anomalies without using such detector output. Instead, only the output signals of detectors that are not saturated are used by the processor 50 for the determination of anomalies.

Alternatively, where the pattern is one for logic and scattered radiation in more or less random directions, it may be useful to compute the minimum or medium values of the detector outputs for detecting anomalies on patterned surfaces. In other words, processor 50 would periodically record samples of the output signals of detectors responding to radiation collected by optical devices arranged at different azimuthal angles about the normal direction 20' (such as scattered radiation passing through the apertures 12*a*, or through the apertures 12*b*) and determines the minimum value of the samples of the outputs from the detectors responding to radiation collected within such apertures. Alternatively, processor 50 may compute a medium value of the detector output samples in response to radiation collected by the optical fibers. In other words, scattered radiation received through the ring of apertures 12*b* simultaneously are detected, and the outputs of all the detectors in response to radiation received through the ring of apertures 12*b* are sampled and the samples are then processed to yield the minimum or medium values of the detector output samples. The same process may be carried out with respect to the first set of apertures 12*a* and their respective fibers and detectors. Processor 50 also communicates with controller 32 (not shown in the figures) to control the motion of the chuck 26 through the controller, and to obtain positional information of the wafer surface in order to associate locations on the surface of the wafer 20 with the output data from the detectors.

While for many applications, the second set of apertures 12*b* may be advantageous to use for the detection of anomalies on patterned surfaces, the first set of apertures 12*a* can also be used for some applications in regard to anomaly detection of patterned surfaces. Thus, if the pattern is somewhat regular, there may be a range of collection angles with respect to the normal direction 20' in which there is no scattering or diffraction from pattern. Thus, the collection apertures 12*a* may be positioned with respect to frame 12 in such manner that no Fourier or other diffraction or scattering from pattern is expected to pass through the collection apertures. In one embodiment, apertures 12*a* may collect radiation at elevation angles between about 5 and 20 degrees from the normal direction 20'. In this manner, the first set of apertures 12*a* will be disposed at elevation angles away from expected components scattered by pattern and would provide to corresponding detectors useful signals for anomaly detection.

From the above, it will be seen that the apparatus of FIGS. 1 and 2 is versatile. It may be used for detecting anomalies on patterned surfaces, unpatterned surfaces and for detecting anomalies caused by chemical and mechanical polishing. The above-described processes may be carried out sequentially or simultaneously. Thus, the laser diodes 14 and 72 may be controlled by processor 50 to emit radiation sequentially so that anomalies on patterned or unpatterned surfaces may first be detected when beam 78 is supplied to the sample. Before or after such operation, processor 50 causes laser diode 14 to emit radiation, and beam 18 is employed to illuminate the sample for the detection of micro-scratches caused by chemical or mechanical polishing. Alternatively, where the two laser diodes 14 and 72 supply radiation of different wavelengths, both diodes may be caused to emit radiation simultaneously, and appropriate filters or dichroic beam splitters (not shown) may be employed so that both types of detection may be carried out simultaneously. As yet another alternative, if a single source such as a laser diode may be employed to emit radiation of two different wavelengths, appropriate dichroic beam splitters may be employed to separate radiation at the two wavelengths into beams 18 and 78 that can be used to illuminate sample 20 simultaneously. Such and other variations are within the scope of the invention.

Where space considerations are not as stringent, the scattered radiation collected by the first set of apertures 12a may be collected and detected in a different manner, as shown in FIG. 5A as an alternative embodiment. Such radiation is first focused by an objective 102 and reflected by a mirror or beam splitter 104 towards a ring of optical fibers 106 shown in FIGS. 5A and 5B. Thus, the optical fibers 106 will collect the radiation that is scattered by the surface that passes through the apertures 12a of FIGS. 1 and 2. Fibers 106 would form substantially a ring around a direction 108 shown in FIG. 5B that corresponds to the normal direction 20' of FIG. 5A and is preferably disposed symmetrically about the direction 108. A source supplies the illumination beam to sample 20 through the beam splitter 104 or by bypassing mirror 104 where a mirror is used; the source and the illumination beam have been omitted in FIG. 5A to simplify the figure. The different components in the embodiment of FIG. 5A may be held in place by a frame such as frame 12 of FIG. 1 or any other suitable means.

FIG. 6 is a cross-sectional view of a section of optical fibers used to collect radiation scattered by the surface and passing through any one of the apertures 12a, 12b and 12c described above. As shown in FIG. 6, each of such fibers preferably includes a core 120, a cladding 122 and an optional external coating 124. The cladding 122 therefore serves as a separator between adjacent optical fiber channels, and reduces crosstalk between adjacent optical fiber channels when they are collecting and conveying radiation scattered by the surface.

While the invention has been described above by reference to various embodiments, it will be understood that changes and modifications may be made without departing from the scope of the invention, which is to be defined only by the appended claims and their equivalent. All references referred to herein are incorporated by reference in their entireties.

What is claimed is:

1. A surface inspection apparatus suitable for use in detecting anomalies on different types of surfaces, said apparatus comprising:
    a source supplying a first and a second beam of radiation to a surface to be inspected, wherein the first beam is substantially normal to the surface and the second beam is at an oblique angle to the surface; and
    optics comprising optical devices at different azimuthal angles about a line normal to the surface or about a direction corresponding thereto, the devices disposed so that radiation scattered by the surface at different azimuthal angles with respect to the line is directed to different devices without employing a common collecting instrument, and at least one collector substantially in a double dark field arrangement relative to the second beam and having an aperture larger than that of any one of the optical devices collecting radiation scattered by the surface.

2. The apparatus of claim 1, said optics comprising a first set of optical devices receiving radiation scattered by the surface in directions near the line, and a second set of optical devices receiving radiation scattered by the surface at low elevation angles to the surface.

3. The apparatus of claim 2, wherein the first set of optical devices comprises 6 to 10 optical devices forming substantially a ring around the line.

4. The apparatus of claim 2, wherein the first set of optical devices receive radiation scattered by the surface at angles between 10 to 30 degrees from the line.

5. The apparatus of claim 2, wherein the second set of devices collect radiation scattered by the surface at a low elevation angle of between 10 and 40 degrees to the surface.

6. The apparatus of claim 2, further comprising a plurality of detectors converting the radiation scattered by the surface and reaching at least some of the devices and the at least one collector into respective signals representative of radiation scattered at different azimuthal angles about the line.

7. The apparatus of claim 6, further comprising a processor determining the presence of anomalies in or on the surface from said signals.

8. The apparatus of claim 1, said optical devices comprising optical fibers, said fibers conveying radiation scattered by the surface and reaching at least some of the devices to the detectors.

9. The apparatus of claim 8, wherein the optical fibers are multimode.

10. The apparatus of claim 1, wherein the second beam illuminates a spot on the surface, and the aperture of the at least one collector subtends an angle of about 20 to 60 degrees at the spot.

11. The apparatus of claim 1, wherein second beam illuminates a spot on the surface, and the aperture of at least one collector subtends an angle of about 40 to 60 degrees from the spot.

12. The apparatus of claim 1, further comprising at least one polarizer in an optical path of the second beam, said polarizer interacting with the second beam before or after the surface interacts with the second beam.

13. The apparatus of claim 12, said at least one polarizer polarizing radiation of the second beam before the beam reaches the surface.

14. The apparatus of claim 13, wherein said at least one polarizer passes P-polarized or circularized polarized radiation, and the at least one collector collects unpolarized radiation scattered by the surface.

15. The apparatus of claim 13, wherein said at least one polarizer passes S-polarized radiation, said apparatus further comprising another polarizer that passes S-polarized radiation and that is located in an optical path of radiation scattered by the surface and collected by the at least one collector.

16. The apparatus of claim 1, said source comprising at least two optical fibers supplying the first and second beams.

17. The apparatus of claim 16, said source further comprising one or more radiation emitting elements supplying the first and second beams.

18. The apparatus of claim 16, said fibers being single-mode fibers.

19. The apparatus of claim 1, said optical devices comprising optical fibers, each of said fibers including a core and cladding, said cladding separating a collection aperture of each fiber from adjacent fiber(s).

20. The apparatus of claim 19, said optical devices further comprising external coatings over the cladding.

21. The apparatus of claim 1, said optical devices disposed symmetrically about the line or the direction.

22. The apparatus of claim 1, said optical devices disposed at elevation angles away from expected components scattered by the pattern.

23. The apparatus of claim 22, wherein said expected components scattered by the pattern are Fourier components.

24. The apparatus of claim 1, wherein said optical devices are substantially at elevation angles between about 5 and 20 degrees from the line or the direction.

25. The apparatus of claim 1, said optics comprising two lenses, wherein apertures of the two lenses are substantially centered at +90 and −90 degrees azimuthal angles relative to a plane of incidence of the second beam.

26. The apparatus of claim 1, said apparatus comprising a compact optical head.

27. The apparatus of claim 1, wherein the compact optical head has dimensions that do not exceed about 5 cm.

28. The apparatus of claim 1, wherein the at least one collector comprises at least one objective focusing radiation scattered by the surface to a detector.

29. The apparatus of claim 1, wherein the at least one collector comprises a plurality of optical fibers collecting radiation scattered by the surface.

30. A method for detecting anomalies on different types of surfaces by means of an apparatus, said apparatus comprising:
a source for a first and a second beam of radiation to a surface to be inspected, wherein the first beam is substantially normal to the surface and the second beam is at an oblique angle to the surface; and
optics comprising optical devices at different azimuthal angles about a line normal to the surface or about a direction corresponding thereto, the devices disposed so that radiation scattered by the surface at different azimuthal angles with respect to the line is directed to different devices, and at least one collector having an aperture larger than that of any one of the optical devices and substantially in a double dark field arrangement relative to the second beam collecting and focusing radiation scattered by the surface; said method comprising:
(a) causing the source to supply the first and second beam to the surface and causing the surface to be scanned by the beam;
(b) directing radiation scattered by the surface to the optical devices without employing a common collecting instrument;
(c) detecting radiation scattered by the surface and collected by the devices and/or the at least one collector; and
(d) determining from the detected radiation anomalies on different types of surfaces.

31. The method of claim 30, wherein said determining determines from the detected radiation anomalies on unpatterned and patterned wafers.

32. The method of claim 30, wherein said determining determines from the detected radiation anomalies on unpatterned or patterned wafers, and wafer surfaces after chemical and mechanical polishing.

33. The method of claim 30, wherein the causing causes the second beam to be supplied to the surface, and the detecting detects radiation scattered by the surface and collected by the at least one collector.

34. The method of claim 33, wherein the causing causes the second beam to be polarized.

35. The method of claim 34, wherein the second beam is caused to be P-polarized and the detecting detects unpolarized radiation for detecting anomalies on smooth surfaces.

36. The method of claim 34, wherein the second beam is caused to be circularly polarized and the detecting detects unpolarized radiation for detecting anomalies on surfaces of dielectric layers.

37. The method of claim 34, wherein the second beam is caused to be S-polarized and the detecting detects S-polarized radiation for detecting anomalies on rough surfaces.

38. The method of claim 33, further comprising:
(e) causing the source to supply the first beam to the surface;
(f) detecting radiation scattered by the surface and collected by the optical devices; and
(g) determining from the detected radiation microscratches on different types of surfaces.

39. The method of claim 38, said optics comprising a first set of optical devices receiving radiation scattered by the surface in directions near the line or the direction, and a second set of optical devices receiving radiation scattered by the surface at low elevation angles to the surface, wherein the detecting in (f) detects radiation scattered by the surface and collected by the first set of optical devices, and wherein said determining comprises comparing signals or pairs of signals converted from radiation received by some of the optical devices in the first set located substantially on opposite sides of the line.

40. The method of claim 39, wherein the detecting in (b) detects radiation scattered by the surface and collected by the second set of optical devices, and wherein said determining in (d) determines from the detected radiation anomalies on patterned or unpatterned surfaces.

41. The method of claim 30, wherein the causing causes the second beam to be supplied to the surface, and the detecting detects radiation scattered by the surface and collected by the optical devices.

42. The method of claim 41, wherein the detecting detects by means of detectors, and the determining determines anomalies without using output signals of detectors that are saturated.

43. The method of claim 41, wherein the detecting comprises sampling outputs of the detectors, and the determining determines anomalies on the surface from minimum or median values of the detector output samples.

44. The method of claim 41, wherein the detecting detects by means of detectors that provide output signals, and the detecting comprises sampling the output signals, and the determining determines anomalies on the surface from minimum or median values of the detector output samples.

45. The method of claim 41, wherein the surface is unpatterned, further comprising selecting from the optical devices only those optical devices that collect radiation scattered by the surface within a predetermined azimuthal collection angle and wherein said detecting in (c) detects only the radiation scattered by the surface and collected by the selected optical devices.

46. A surface inspection apparatus suitable for use in detecting anomalies on different types of surfaces, said apparatus comprising:

a source supplying a first or a second beam of radiation to a surface to be inspected, wherein the first beam is substantially normal to the surface and the second beam is at an oblique angle to the surface; and optics comprising optical devices at different azimuthal angles about a line normal to the surface or about a direction corresponding thereto, the devices disposed so that radiation scattered by the surface at different azimuthal angles with respect to the line is directed to different devices without employing a common collecting instrument, and at least one collector substantially in a double dark field arrangement relative to the second beam and having an aperture larger than that of any one of the optical devices collecting radiation scattered by the surface.

47. The apparatus of claim 46, said optics comprising a first set of optical devices receiving radiation scattered by the surface in directions near the line, and a second set of optical devices receiving radiation scattered by the surface at low elevation angles to the surface.

48. The apparatus of claim 47, wherein the first set of optical devices comprises 6 to 10 optical devices forming substantially a ring around the line.

49. The apparatus of claim 47, wherein the first set of optical devices receive radiation scattered by the surface at angles between 10 to 30 degrees from the line.

50. The apparatus of claim 47, wherein the second set of devices collect radiation scattered by the surface at a low elevation angle of between 10 and 40 degrees to the surface.

51. The apparatus of claim 47, further comprising a plurality of detectors converting the radiation scattered by the surface and reaching at least some of the devices and the at least one collector into respective signals representative of radiation scattered at different azimuthal angles about the line.

52. The apparatus of claim 51, further comprising a processor determining the presence of anomalies in or on the surface from said signals.

53. The apparatus of claim 52, the source supplying the first beam and not the second beam of radiation to the surface, wherein the processor processes signals converted from radiation received by the first set of optical devices to determine the presence of defects on a semiconductor wafer surface after it has been chemically and mechanically polished.

54. The apparatus of claim 53, wherein the processor compares signals or pairs of signals converted from radiation received by some of the optical devices in the first set located substantially on opposite sides of the line, to determine the presence of micro-scratches on the semiconductor wafer surface after it has been chemically and mechanically polished.

55. The apparatus of claim 46, said optical devices comprising optical fibers, said fibers conveying radiation scattered by the surface and reaching at least some of the devices to the detectors.

56. The apparatus of claim 55, wherein the optical fibers are multimode.

57. The apparatus of claim 46, wherein the second beam illuminates a spot on the surface, and the aperture of the at least one collector subtends an angle of about 20 to 60 degrees at the spot.

58. The apparatus of claim 46, wherein second beam illuminates a spot on the surface, and the aperture of at least one collector subtends an angle of about 40 to 60 degrees from the spot.

59. The apparatus of claim 46, further comprising at least one polarizer in an optical path of the second beam, said polarizer interacting with the second beam before or after the surface interacts with the second beam.

60. The apparatus of claim 59, said at least one polarizer polarizing radiation of the second beam before the beam reaches the surface.

61. The apparatus of claim 60, wherein said at least one polarizer passes P-polarized or circularized polarized radiation, and the at least one collector collects unpolarized radiation scattered by the surface.

62. The apparatus of claim 60, wherein said at least one polarizer passes S-polarized radiation, said apparatus further comprising another polarizer that passes S-polarized radiation and that is located in an optical path of radiation scattered by the surface and collected by the at least one collector.

63. The apparatus of claim 46, said source comprising at least two optical fibers supplying the first and second beams.

64. The apparatus of claim 63, said source further comprising one or more radiation emitting elements supplying the first and second beams.

65. The apparatus of claim 63, said fibers being single-mode fibers.

66. The apparatus of claim 46, said optical devices comprising optical fibers, each of said fibers including a core and cladding, said cladding separating a collection aperture of each fiber from adjacent fiber(s).

67. The apparatus of claim 66, said optical devices further comprising external coatings over the cladding.

68. The apparatus of claim 46, said optical devices disposed symmetrically about the line or the direction.

69. The apparatus of claim 46, said optical devices disposed at elevation angles away from expected components scattered by the pattern.

70. The apparatus of claim 69, wherein said expected components scattered by the pattern are Fourier components.

71. The apparatus of claim 46, wherein said optical devices are substantially at elevation angles between about 5 and 20 degrees from the line or the direction.

72. The apparatus of claim 46, said optics comprising two lenses, wherein apertures of the two lenses are substantially centered at +90 and −90 degrees azimuthal angles relative to a plane of incidence of the second beam.

73. The apparatus of claim 46, said apparatus comprising a compact optical head.

74. The apparatus of claim 46, wherein the compact optical head has dimensions that do not exceed about 5 cm.

75. The apparatus of claim 46, wherein the at least one collector comprises at least one objective focusing radiation scattered by the surface to a detector.

76. The apparatus of claim 46, wherein the at least one collector comprises a plurality of optical fibers collecting radiation scattered by the surface.

77. A method for detecting anomalies on different types of surfaces by means of an apparatus, said apparatus comprising:

a source for a first or a second beam of radiation to a surface to be inspected, wherein the first beam is substantially normal to the surface and the second beam is at an oblique angle to the surface; and optics comprising optical devices at different azimuthal angles about a line normal to the surface or about a direction corresponding thereto, the devices disposed so that radiation scattered by the surface at different azimuthal angles with respect to the line is directed to different devices, and at least one collector having an aperture larger than that of any one of the optical devices and substantially in a double dark field arrangement relative to the second beam collecting and focusing radiation scattered by the surface; said method comprising:
- (a) causing the source to supply the first or second beam to the surface and causing the surface to be scanned by the beam;
- (b) directing radiation scattered by the surface to the optical devices without employing a common collecting instrument;
- (c) detecting radiation scattered by the surface and collected by the devices and/or the at least one collector; and
- (d) determining from the detected radiation anomalies on different types of surfaces.

78. The method of claim 77, wherein said determining determines from the detected radiation anomalies on unpatterned and patterned wafers.

79. The method of claim 77, wherein said determining determines from the detected radiation anomalies on unpatterned or patterned wafers, and wafer surfaces after chemical and mechanical polishing.

80. The method of claim 77, wherein the causing causes the second beam to be supplied to the surface, and the detecting detects radiation scattered by the surface and collected by the at least one collector.

81. The method of claim 80, wherein the causing causes the second beam to be polarized.

82. The method of claim 81, wherein the second beam is caused to be P-polarized and the detecting detects unpolarized radiation for detecting anomalies on smooth surfaces.

83. The method of claim 81, wherein the second beam is caused to be circularly polarized and the detecting detects unpolarized radiation for detecting anomalies on surfaces of dielectric layers.

84. The method of claim 81, wherein the second beam is caused to be S-polarized and the detecting detects S-polarized radiation for detecting anomalies on rough surfaces.

85. The method of claim 80, further comprising:
- (e) causing the source to supply the first beam to the surface;
- (f) detecting radiation scattered by the surface and collected by the optical devices; and
- (g) determining from the detected radiation microscratches on different types of surfaces.

86. The method of claim 85, said optics comprising a first set of optical devices receiving radiation scattered by the surface in directions near the line or the direction, and a second set of optical devices receiving radiation scattered by the surface at low elevation angles to the surface, wherein the detecting in (f) detects radiation scattered by the surface and collected by the first set of optical devices, and wherein said determining comprises comparing signals or pairs of signals converted from radiation received by some of the optical devices in the first set located substantially on opposite sides of the line.

87. The method of claim 86, wherein the detecting in (b) detects radiation scattered by the surface and collected by the second set of optical devices, and wherein said determining in (d) determines from the detected radiation anomalies on patterned or unpatterned surfaces.

88. The method of claim 77, wherein the causing causes the second beam to be supplied to the surface, and the detecting detects radiation scattered by the surface and collected by the optical devices.

89. The method of claim 88, wherein the detecting detects by means of detectors, and the determining determines anomalies without using output signals of detectors that are saturated.

90. The method of claim 88, wherein the detecting comprises sampling outputs of the detectors, and the determining determines anomalies on the surface from minimum or median values of the detector output samples.

91. The method of claim 88, wherein the detecting detects by means of detectors that provide output signals, and the detecting comprises sampling the output signals, and the determining determines anomalies on the surface from minimum or median values of the detector output samples.

92. The method of claim 88, wherein the surface is unpatterned, further comprising selecting from the optical devices only those optical devices that collect radiation scattered by the surface within a predetermined azimuthal collection angle and wherein said detecting in (c) detects only the radiation scattered by the surface and collected by the selected optical devices.

* * * * *